United States Patent
Kirchner (10) Patent No.: US 7,267,662 B1
(45) Date of Patent: Sep. 11, 2007

(54) MILK SUCKING PUMP

(75) Inventor: Claudia Kirchner, Markgröningen (DE)

(73) Assignee: KaWeCo GmbH, Ditzingen (DE)

(*) Notice: Subject to any disclaimer, the term of this patent is extended or adjusted under 35 U.S.C. 154(b) by 0 days.

(21) Appl. No.: 10/049,209

(22) PCT Filed: May 25, 2000

(86) PCT No.: PCT/EP00/04758

§ 371 (c)(1),
(2), (4) Date: Feb. 5, 2002

(87) PCT Pub. No.: WO01/34226

PCT Pub. Date: May 17, 2001

(30) Foreign Application Priority Data

Nov. 11, 1999 (DE) ................. 199 54 112

(51) Int. Cl.
*A61M 1/06* (2006.01)
(52) U.S. Cl. .................................. 604/74 A
(58) Field of Classification Search ............. 604/65, 604/66, 67, 74, 346, 315, 184, 533, 76, 75; D24/109
See application file for complete search history.

(56) References Cited

U.S. PATENT DOCUMENTS

| | | | |
|---|---|---|---|
| 790,051 A | 5/1905 | Halstead | |
| 3,782,385 A | 1/1974 | Loyd | |
| 4,583,970 A * | 4/1986 | Kirchner | 604/74 |
| 4,813,932 A | 3/1989 | Hobbs | |
| 5,007,899 A | 4/1991 | Larsson | |
| 5,415,632 A * | 5/1995 | Samson | 604/74 |
| 5,542,921 A * | 8/1996 | Meyers et al. | 604/74 |
| 5,749,850 A * | 5/1998 | Williams et al. | 604/74 |
| 5,810,772 A * | 9/1998 | Niederberger | 604/74 |
| 5,843,029 A * | 12/1998 | Bachman et al. | 604/74 |
| 6,042,560 A | 3/2000 | Niederberger | |
| 6,152,896 A | 11/2000 | Bachman et al. | |
| D446,300 S | 8/2001 | Kirchner | |
| 6,299,594 B1 | 10/2001 | Silver | |

FOREIGN PATENT DOCUMENTS

| | | |
|---|---|---|
| DE | 87 14 995 | 12/1987 |
| EP | 330 845 | 9/1989 |
| EP | 385 933 | 9/1990 |
| EP | 733 376 | 9/1996 |

* cited by examiner

*Primary Examiner*—Nicholas D. Lucchesi
*Assistant Examiner*—Christopher D. Koharski
(74) *Attorney, Agent, or Firm*—Pauley Petersen & Erickson (57) ABSTRACT

A milk sucking pump having a top component with a breast joining piece and which is or can be detachably fixed to the opening of a container and a hand pump unit that is detachably connected thereto by a connecting branch or a connecting bore. The hand pump unit has a cap-like connection section and a pump piston which can be moved to and from in a piston-swept volume by a rotatable actuating handle that has a return mechanism. This invention provides a simple construction and good handling. The cap-like connection section and the piston-swept volume are combined to form a uniform cap component which is fixed to the top component. The return mechanism acts upon the actuating lever and is mounted on the cap component.

43 Claims, 7 Drawing Sheets

MILK SUCKING PUMP

This U.S. Patent Application claims domestic priority under 35 U.S.C. § 371, of PCT/EP00/04758, filed 25 May 2000, and also claims foreign priority under 35 U.S.C. § 119, of German Priority Document 199 54 112.4, filed on 11 Nov. 1999.

BACKGROUND OF THE INVENTION

1. Field of the Invention

This invention relates to a breast pump with an attachment, which can be releasably applied to the opening of a container and has a breast attachment element, and with a manual pump unit, which is releasably connected to the attachment by a connecting sleeve or a connecting bore, which has a cap-shaped connecting section, as well as a pump piston, which can be moved back and forth in a stroke chamber by an actuating handle that is pivotable and has a retracting mechanism.

2. Description of Related Art

A known breast pump with a manual pump unit is disclosed in German Patent Reference DE 87 14 995 U1. With this known breast pump, an attachment with a funnel-shaped breast attachment element and with a pump connector is releasably screwed to a container. A cap-shaped section of the manual pump unit is placed on the pump connecting element. A pump cylinder with a guided pump piston in an interior is attached, horizontally projecting to the rear, to the cap-like section. The pump piston is moved back and forth with a lever-shaped actuating handle wherein, for returning the pump piston, the handle is supported by a U-shaped spring on a support fastened underneath the pump cylinder which extends as far as the underside of the container. The construction of the manual pump unit is relatively bulky and cumbersome, so that there is one disadvantage in manipulating it.

In another breast pump represented in European Patent Reference EP 0 330 845 A2, a manual pump unit has a manual actuating element, which axially extends out of the pump cylinder toward the rear and is moved by one hand in an axial direction, while the breast pump is held with other hand. Thus, both hands are required for manipulation.

A pump cylinder of a breast pump is shown in European Patent Reference EP 0 385 933 A2 is oriented obliquely upward. A pump piston, guided in its interior, is actuated by two actuating elements, which are conducted laterally along the pump cylinder, and by a transverse strip, which is hingedly fastened on the actuating elements above the pump cylinder and moves upward when the actuating element is pressed together at the center, and downward, when it is released, in order to move the pump piston back and forth. The actuating unit and the pump piston can be replaced by an electrical pump, which is connected by a cover, which can be placed on the top of the pump cylinder.

SUMMARY OF THE INVENTION

One object of this invention is to provide a breast pump of the type mentioned above but which has improved manipulation along with a simplified construction.

This object is achieved with a pump having characteristics described in this specification and in the claims. A cap-shaped connecting section and a stroke chamber are combined in a mutual cap element, which is fixed on an attachment by a retaining device. A retracting mechanism, one side of which acts on the actuating handle, is seated with the other side on the cap element.

Simple cleaning and manipulation are possible because in the completely inserted state of the pump piston, a stroke chamber opening on the side of the stroke chamber facing away from the breast connection element is covered by an upper section of the actuating handle which, in the position of use, is located above a pivot axis.

An easy movement of the piston and the connected actuation elements, which is free of wear to a considerable extent over time, is achieved because the stroke chamber in the cap element is curved in an arc-shape according to a movement path of the pump piston, which is actuated by an upper section of the actuating handle.

The entry of air into the piston chamber and the pumping output are assisted because with the container attached, a pivot path of the upper section of the actuating handle in the area of its connection to the pump piston is selected to be so large that, in the moved-out state, at least an upper edge section of the pump piston is outside of an upper opening edge of the stroke chamber opening. In a similar manner it is possible to cut, for example, a groove, or a bore, or the like, into the piston wall.

A simple, well functioning retracting mechanism is created and cleaning is easier because the retracting mechanism has at least one tension spring and a suspension element is positioned on the actuating handle. A further suspension element is positioned on the cap element so that with the piston in the inserted position, the direction of the tensile force lies above the pivot axis of the actuating handle, at least until, with the container attached, the actuating handle reaches its maximum pivot angle in the retraction direction of the pump piston. With the container removed and with a further increased pivot angle the direction of the tensile force lies below the pivot axis, so that the actuating handle is maintained in the opened position relative to the cap element.

In one embodiment of a well functioning, simple retracting mechanism, the retracting mechanism has at least one pressure spring. A support element on the inside of the actuating handle and a support section at the cap element are positioned so that, at least with the piston rod inserted, the direction of the force of pressure lies below the pivot axis of the actuating handle. A rubber block, a spiral spring or a spring, for example, can be used.

A restoring force which remains stable over time is achieved because the pressure spring is embodied as a spiral spring with front suspension lug suspended and retained in a support section of a free end section of the retaining element, which is oriented downward when in use, and arcs upward in a U-shape in an interior chamber of the cap element and the grip and is supported with a free end section bent off from the suspension lug on a support element arranged on the inside of the actuating handle. In this embodiment the support section and the support element are formed on the retaining element, or on the actuating handle. The spiral spring, which for example is made of steel, is thermally stable and can be boiled clean. The spiral spring can be simply mounted and can be easily housed so it is invisible.

The manual pump unit can be easily replaced by an electric pump directly connected by a hose to the connecting sleeve arranged on the attachment or to the connecting bore.

Simple sealing, which promotes a good pumping output, is achieved with the connecting point between the connecting sleeve or the connecting bore and the cap element sealed by a conical connection or of a seal ring.

During electrical operation, if the electric pump does not have automatic ventilation, ventilation can be manually regulated. An opening is provided on the attachment in the area of the connecting sleeve or the connection bore, which can be closed by a stopper or, when the stopper is removed, can be closed by hand.

A simple, releasable coupling between the attachment and the manual pump unit is achieved because the retaining means have a snap-in element which snaps together with the attachment, when the cap element is coupled to the attachment. Design and operation are simplified. The snap-in element is embodied as a snap-in tongue, oriented toward the container with a free end section and which, in the attached state, extends with a snap-in section behind an edge of the attachment facing toward the container when the cap element, located opposite the snap-in tongue, is pushed on the connecting sleeve or the connecting bore oriented axis-parallel in relation to the container.

Operation is easier because on its interior the cap element has retaining flaps or ribs on both sides, which form guide elements when placed on the attachment and securing elements against twisting of the cap element in relation to the attachment.

Because seating elements are arranged on both lateral sections of the cap element and on both lateral sections of the actuating handle which, in the form of separable bearing pin/bearing eye connection, form the pivot axis between the actuating handle and the cap element, there is simple construction and simple operation.

A shape of the manual pump unit which is advantageous for cleaning and handling, has in the rear area remote from the breast attachment element a cap element with a rounded top which, in the pivoted-in state of the upper section of the actuating handle, makes a steady transition into the curved exterior of the latter.

The operation of the manual pump is easier because in cross section the upper section and the lower section are outwardly rounded on a rear side facing away from the breast attachment element and make a steady transition into each other. An obtuse angle, open toward the rear, is formed between the upper section and the lower section.

A simple change of the pump output is achieved because there is an intermediate piece which can be inserted into a V-shaped gap which, when the actuating handle is pivoted, is formed in the upper area between the upper section of the actuating handle and the edge of the stroke chamber opening. Thus the stroke travel of the pump piston can be preset to be continuous or stepped.

The spacer cams, which contact the upper edge of the container in the attached stage, are on the inside of a screw connector of the attachment for connecting it with the container. An air exchange with the atmosphere is provided in the attached state, and the ventilation of the container is assured when the attachment is screwed on the container.

To attach the pump piston in a simple manner, the pump piston has a piston rod formed on the pump piston, centered or eccentric, on which backward oriented end section a releasable hinged connection with the upper section of the actuating handle is provided.

If a protrusion made of a soft material is arranged on the interior, on the container side, of the lower section of the actuating handle for forming a stop between the actuating handle and the container, the hard contact of the actuating handle with the container wall is prevented. Here, the stop can also be designed for changing the pivot path for actuating the pump piston.

There is good handling because the manual pup unit and the attachment are arranged so their weight is compensated. In an empty state and with the attachment placed on it and the manual pump unit attached, the container remains upright.

The interior of the breast pump can be variably ventilated by a secondary air regulating unit, which can be operated manually from the outside, on the cap element for ventilating the suction chamber, which varies during the pump operation.

There is a simple construction and easy manipulation because the secondary air regulating unit has a rotatable insert and/or attachment arranged on the exterior of the cap element, by which rotation a flow-through conduit, which leads through a wall in the cap element into the stroke chamber, is opened to a greater or lesser extent, or can be completely closed. In this case the setting preferably is continuous and can be reproduced, for example, with markings which can be felt. A vacuum is automatically reduced when the flow-through conduit is open, and the degree of the vacuum is individually selected. It is advantageous for health care reasons, if it is produced from silicon.

BRIEF DESCRIPTION OF THE DRAWINGS

This invention is explained in greater detail in view of an exemplary embodiment, wherein the drawings show.

DESCRIPTION OF PREFERRED EMBODIMENTS

As shown in FIG. 1, the breast pump 1 has a container for receiving pumped out milk, an attachment 6 screwed on the container 2, a manual pump unit 3 releasably attached to the latter, having an actuating handle 4 and a cap element 5, releasably connected with the cap element 5.

The attachment 6 is screwed by means of a screw connector 6.2 to a collar section of the container 2, which surrounds the container opening. A breast attachment element 6.1 is connected in a known manner to a cover section of the screw connector 6.2, wherein a flow-through valve is arranged approximately in the area of the cover element, through which the pumped milk reaches the container 2 and is prevented from exiting the container 2, or cannot be aspirated back.

Figure 2A:
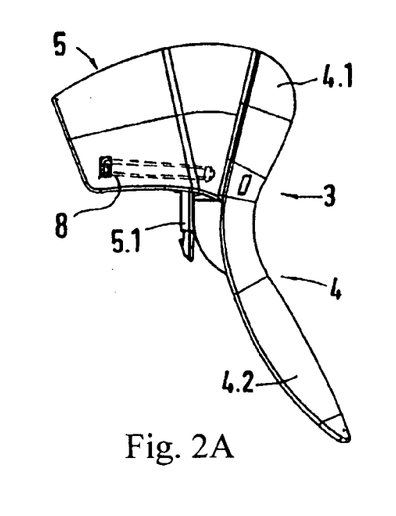
FIGS. 2A to 2E as views of a manual pump unit employed with the breast pump in a side view, a rear view, a front view, a top view, and in a perspective representation.
Figure 2B:
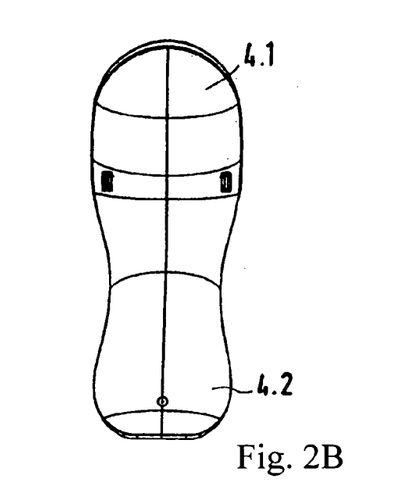
Figure 2C:
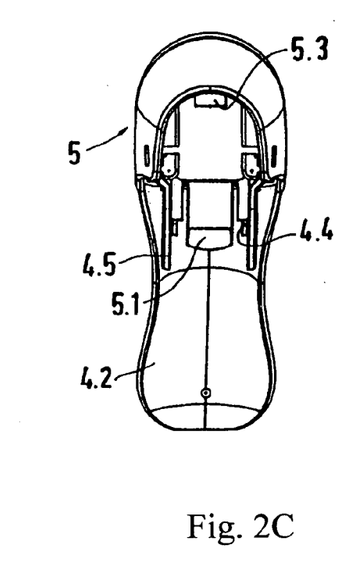
Figure 2D:
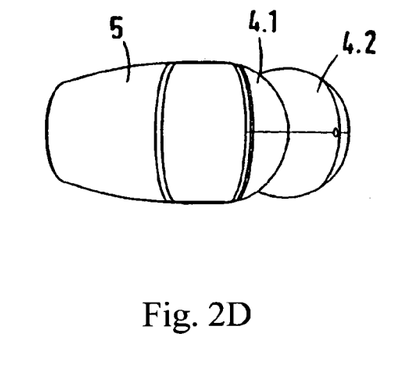
Figure 2E:
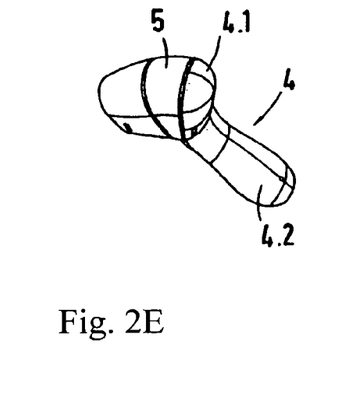
Figure 3A:
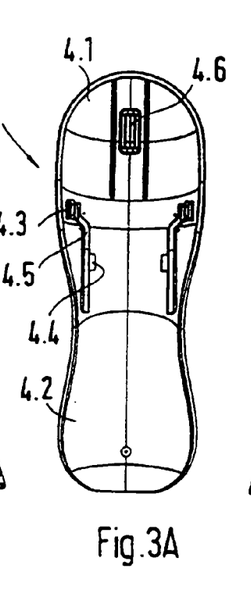
FIGS. 3A to 3F as views of an actuating handle employed with the breast pump from a front, a right side, a left side, a rear, a bottom and a top.
Figure 3B:
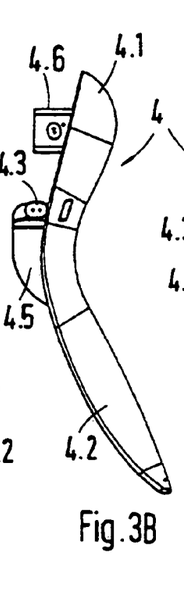
Figure 3C:
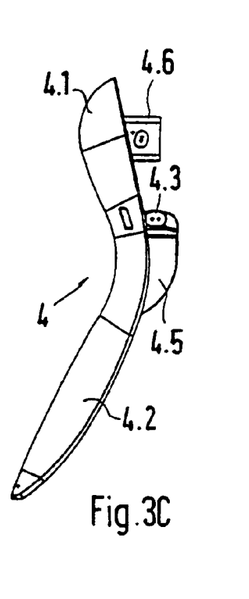
Figure 3D:
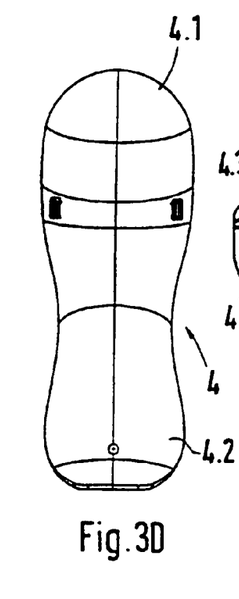
Figure 3E:
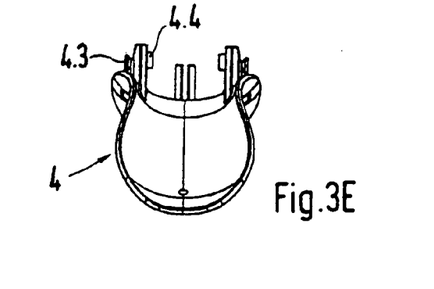
Figure 3F:
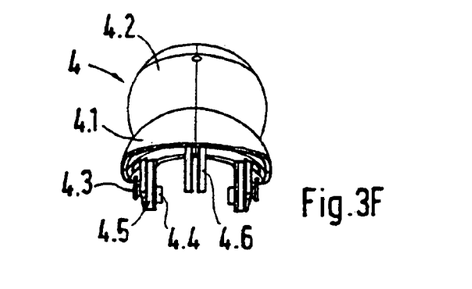
Figure 4A:
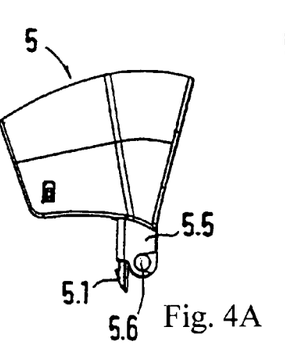
FIGS. 4A to 4F as views of a cap element employed with the breast pump from a side, a rear, a front, a bottom, a top and in a perspective view.
Figure 4B:
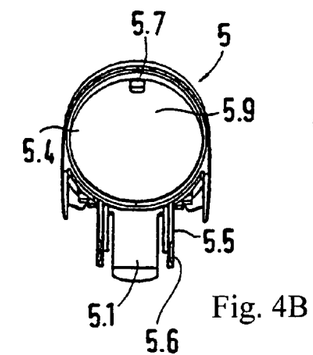
Figure 4C:
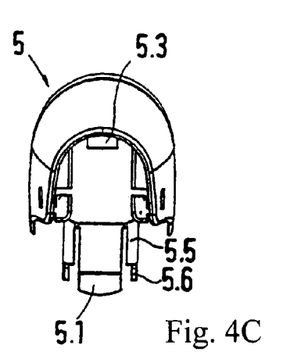
Figure 4D:
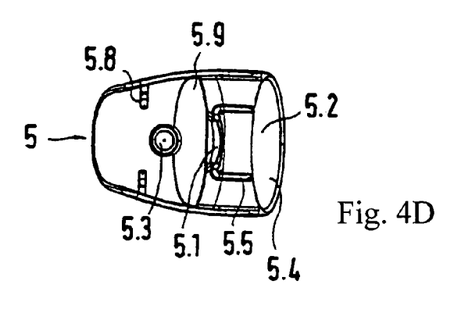
Figure 4E:
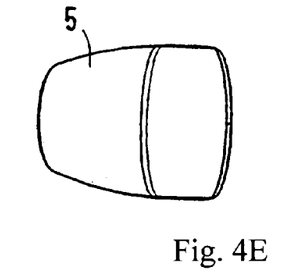
Figure 4F:
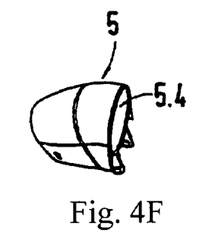
Figure 5A:
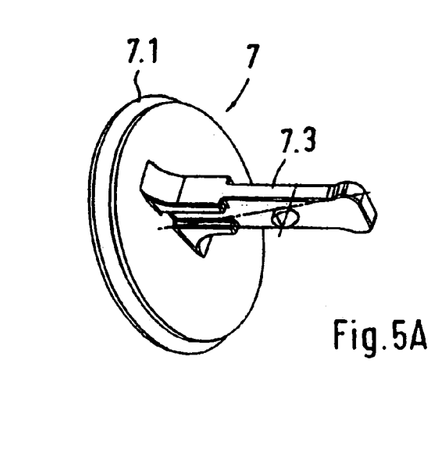
FIGS. 5A to 5E as views of a pump piston employed with the breast pump in a perspective, a top, a side, a rear, and a front.
Figures 5B, 5C, 5E:
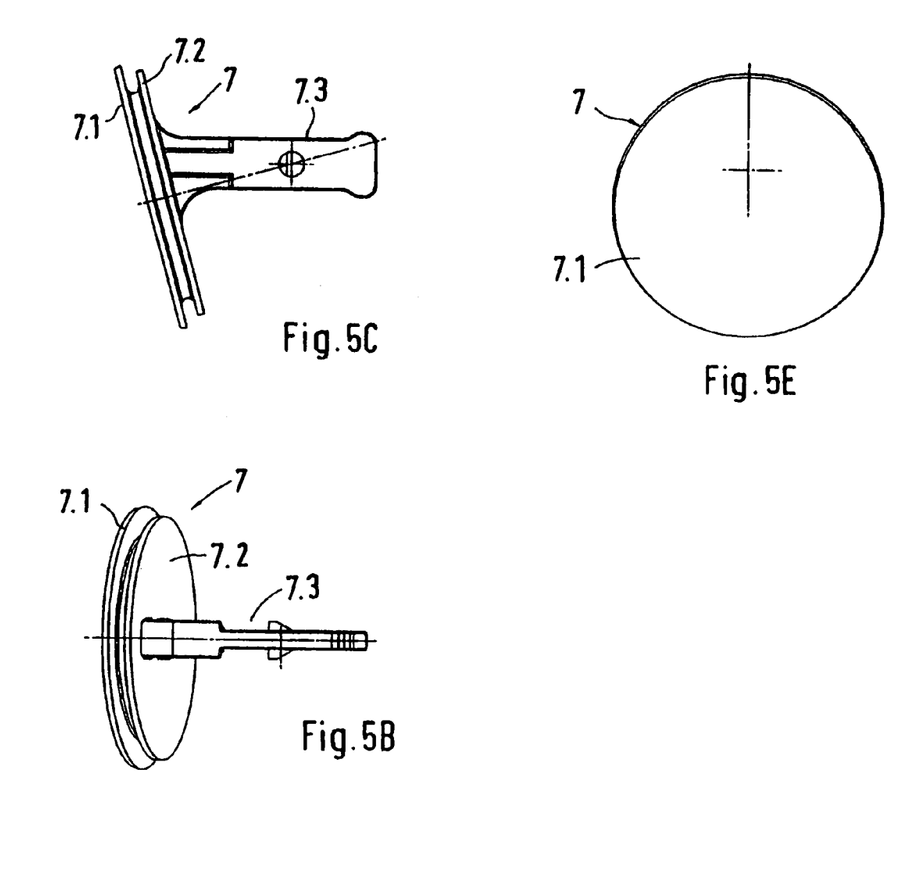
Figure 5D:
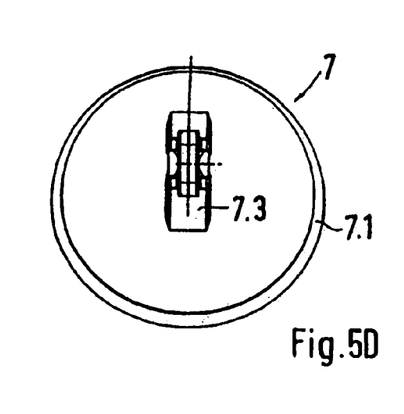

On the attachment 6, the manual pump unit 3 with the cap element 5 is tightly placed on a connecting element in the form of a sleeve which projects upward parallel with the container axis and has an appropriately matched coupling element 5.3, which is sealed, for example, by means of a cone seal or an additional sealing element and is shown in FIGS. 2C, 4C and 4D. The coupling element 5.3 is formed on the inside of the upper wall of the cap element 5, extending downward, and makes a transition into a connecting conduit 5.7, which terminates in a stroke chamber also formed in the cap element 5, as shown in FIG. 4B. A retaining element 5.1 in the form of a snap-in tongue projects from the underside of the cap element 5, which snaps into a snap-in shoulder at the lower edge of the screw connector 5.2, wherein the snap-in tongue is displaced against its spring force by means of a snap-in ramp at the end, when the cap element 5 is attached.

The stroke chamber 5.2 is arranged in the rear section of the cap element 5 facing away from the attachment element 6.1 and has a stroke chamber opening 5.4 on its rear, while it is closed off toward the front with a front face 5.9. The stroke chamber 5.2 is designed to be curved in accordance with the movement path of a pump piston 7, which is moved back and forth therein with the actuating handle 4. Retaining flaps, or retaining strips 5.5 of a retaining element which is U-shaped in cross section, are provided on the underside of the cap element 5 at the side, and have in their lower area near the free end bearing eyes 5.6 for the insertion of correspondingly designed bearing pins 4.4 of the actuating handle 4 in order to make a releasable, hinged connection of the actuating handle 4 on the cap element 5. Strips extending essentially parallel with the container axis, are formed on both sides of the interior of the front section of the cap element 5, as well as suspension elements 5.8, in which retracting springs 8, for example rubber rings, are suspended, in order to bring, by means of a spring force, the actuating handle 4 attached to the cap element 5 after its deflection back into the initial position, in which the pump piston 7 is introduced into the stroke chamber 5.2, as shown in FIG. 2A. Corresponding further suspension elements 4.3 are attached to strips 4.5 on the inside of the actuating handle 4. The strips 4.5 also support the bearing pins 4.4, as shown in FIGS. 2C, 3A, 3E and 3F.

Figures 1A, 1C:
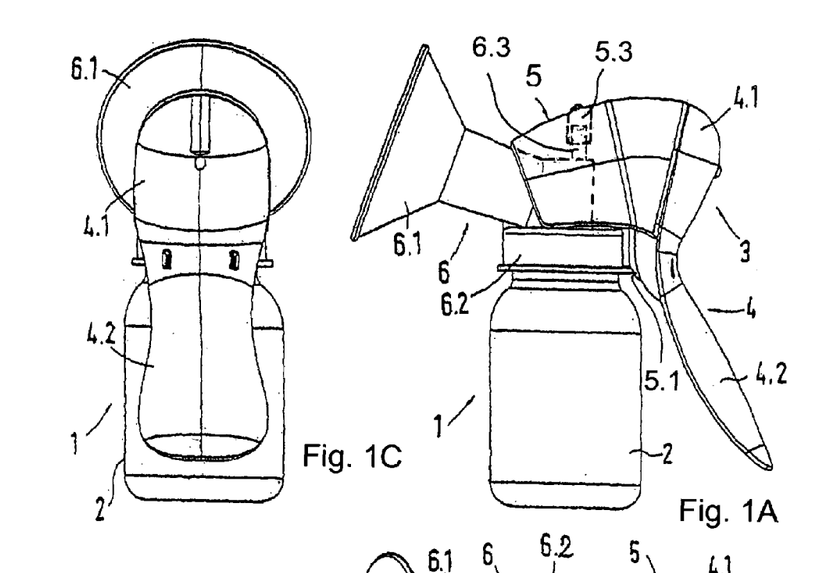
FIGS. 1A to 1E as views of a breast pump with a container from the front, the rear, above, and in a perspective representation.
Figure 1B:
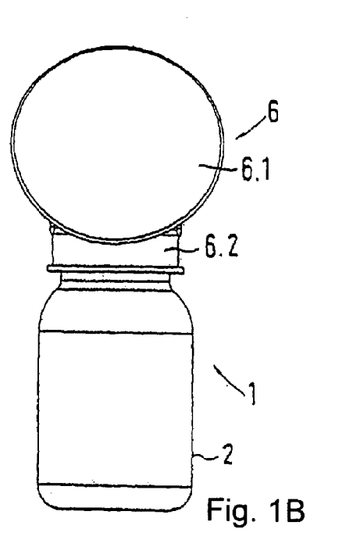
Figures 1D, 1E:
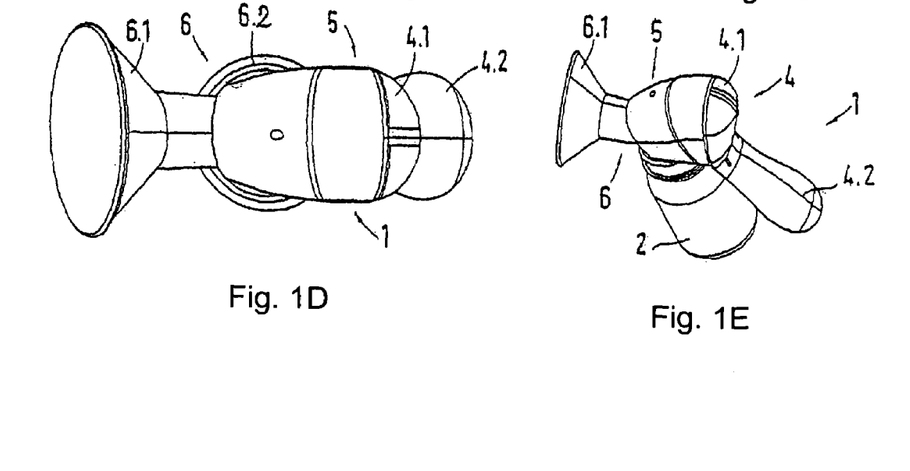
Figure 1F:
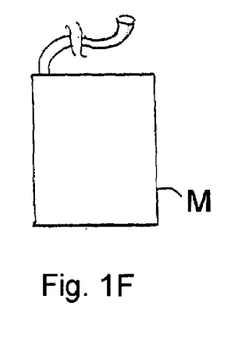
FIG. 1F shows a diagrammatic view of an electric motor that can be attached to a connecting sleeve of a breast pump.

With its upper section 4.1, which is located above the hinge axis, the actuating handle 4 makes a steadily curving transition at the top and the sides into the curves of the cap element 5. In the completely inserted position of the pump piston 7, it closes the stroke chamber 5.4, as shown in FIGS. 1A and 2A. A lower section 4.2, oriented backward at an obtuse angle, which in cross section is also convexly curved outward, follows the upper section 4.1 of the actuating handle 4 approximately in the area of the pivot axis, so that satisfactory manipulation of the lower handle section 4.2 for performing a pumping operation results. The lower section 4.2 rests against the ball of the thumb, and in the transition area between the upper section 4.1 and the lower section 4.2, the thumb and index finger, pointing forward, can grasp the upper container section. A connecting element 4.6 is formed on the inside of the upper section 4.1 for providing a connection with a piston rod 4.3 of the pump piston 7. As shown in FIGS. 5A to 5D, the piston rod 4.3 is formed on a retainer plate 7.2, which forms a part of a piston plate 7.1 with lateral sealing edges. A soft spacer element, not shown, can be provided on the inside in the lower section 4.2 of the actuating handle, so that during actuation the lower section 4.2 gently touches the outside of the container 2, and so that a limitation of the stroke travel of the pump piston 7 can thus be set. Moreover, an intermediate piece, not shown, can be provided for limiting the stroke travel and therefore the pumping effect which, during the pivoting out of the upper section 4.1 of the actuating handle 4, can be inserted between the edge of the stroke chamber opening 5.4 and the upper section 4.1. An opening, which can be selectively released and can be closed by means of a stopper, can be provided on the back of the attachment 2 for manual ventilation when an electric pump is attached to the connecting sleeve.

FIGS. 6A to 6E, 7A, and 7B show a further embodiment of the breast pump 1, wherein the manual pump unit 3 has a secondary air regulating unit 9 and a retracting mechanism 8', which is an alternative to the previous exemplary embodiments. Otherwise the design essentially corresponds to that of the previous embodiment, wherein the reference numerals relate to corresponding parts of the breast pump 1.

Figures 6A, 6B, 6C:
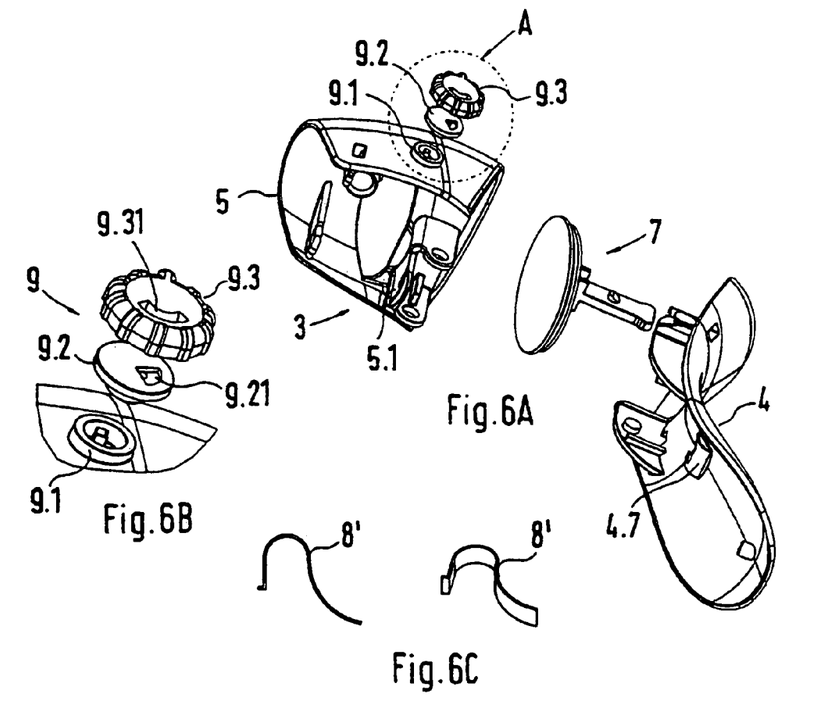
FIGS. 6A to 6E as views of a further manual pump unit, in which a different retracting mechanism and a secondary air regulating unit are provided in contrast to the previous exemplary embodiments.
Figure 6D:
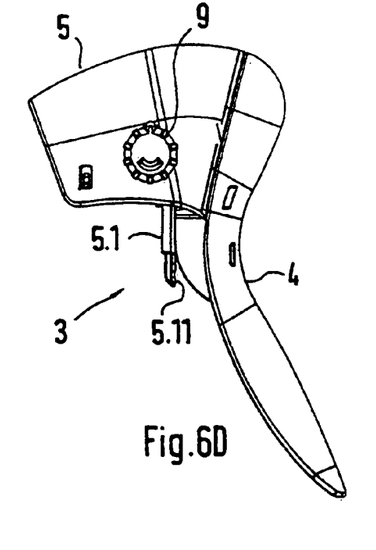
Figure 6E:
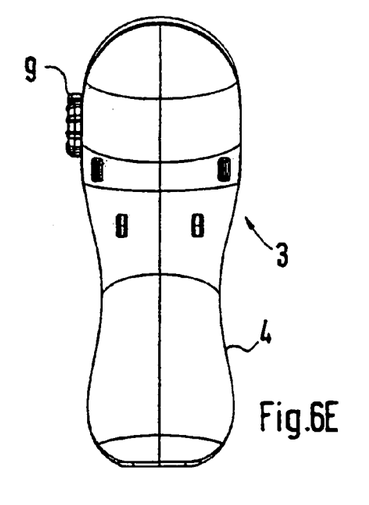

The retracting mechanism shown in FIGS. 6A and 6C has a spiral spring 8', which is essentially bent into a U-shape, wherein the end of one front leg is angled off to form a suspension lug, while the other leg terminates in an outwardly bent end section. The suspension lug is fixed in a cutout formed in the lower end section, in the position of use, of the retaining element 5.1 in the shape of a support section 5.11, which is formed during the manufacturing process. The other leg end is inserted and supported in a support element 4.7 formed on the inside of the actuating handle 4. The spiral spring can be easily mounted and removed, for example while disassembling the cap element 5 and the actuating handle 4. The spiral spring is preferably embodied as a steel spring and maintains its spring properties permanently and can also be cleaned by boiling. In the installed state it projects with the U-shaped arch upward into a hollow space formed between the cap element 5 and the actuating handle 4, so that it is housed in a hidden manner.

Figure 7A:
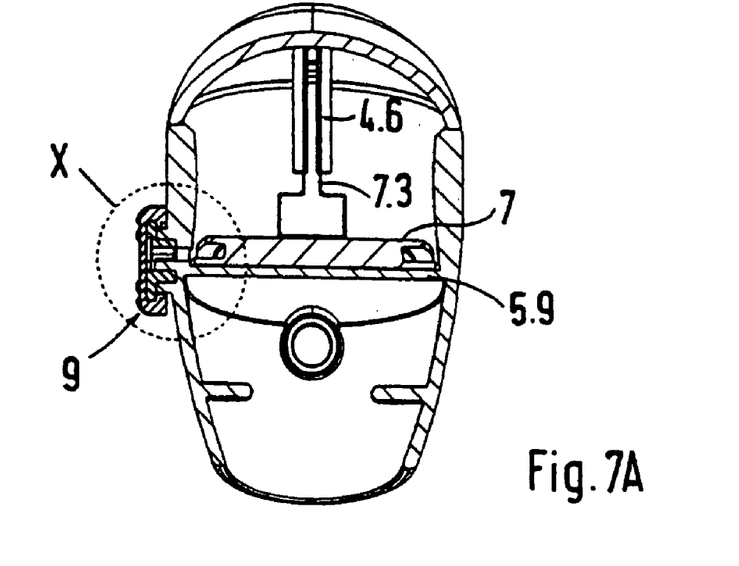
FIGS. 7A and 7B as views of a cross section through the manual pump unit in accordance with FIGS. 6A, 6D and 6E in a bottom view, or in a detailed view.
Figure 7B:
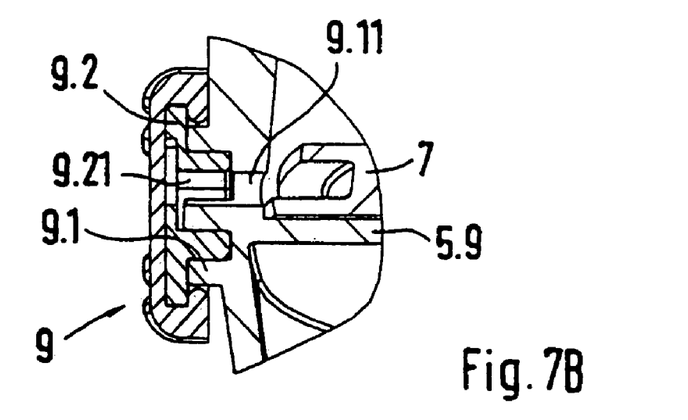

As shown in FIGS. 6A, 6B, 6E, 6D, 7A and 7B, the secondary air regulating unit 9 is arranged laterally on the exterior of the wall of the cap element 5. It has an inlet section 9.1, which is formed in the cap element 5 and slightly projects outward, in which a central receiving pin for an insert 9.2, which can be attached from the outside, as well as a flow-through conduit 9.11, which terminates in the stroke chamber 5.2 in the vicinity of the front wall 5.9, are provided, as shown in FIGS. 7A and 7B. An opening 9.21 is formed in the insert 9.2, which is aligned or can be aligned with the flow-through conduit 9.11. The inlet section 9.1 and the insert 9.2 are covered by a removable cover 9.3, preferably made of silicon, wherein a slot 9.31 can be more or less aligned with the opening 9.21. The opening 9.21 terminates in a laterally widened section, so that the amount of the covering of the conduit leading outward from the stroke chamber 5.2 can be easily varied within a wide range by an appropriate rotation of the cover 9.3. For simple actuation, the cover 9.3 has grip elements, which project rib-like from the circumference, one of which is thickened for marking a position of rotation. As shown in FIG. 7B, a lip-like edge of the cover 9.3 extends below an outward projecting circumferential collar of the inlet section 9.1, so that satisfactory retention and sealing of the cover 9.3 result.

The secondary air regulation unit 9 provides a continuous, reproducible regulating possibility for air conducted into the suction chamber of the breast pump. A built-up vacuum is automatically reduced by means of the secondary air opening being opened to a greater or lesser extent, and the size of the vacuum can be individually selected. Automatically intermittent pumping can be performed.

The invention claimed is:

1. In a breast pump having an attachment releasably applied to an opening of a container and having a breast attachment element and a manual pump unit which is releasably connected to the attachment by a connecting sleeve or a connecting bore having a cap-shaped connecting section, and a pump piston which can be moved back and forth in a stroke chamber with an actuating handle, which is pivotable and has a retracting mechanism, the improvement comprising:

the cap-shaped connecting section and the stroke chamber combined in a mutual cap element, which is fixed on the attachment by a retaining means having a snap-in element snapped together with the attachment when the cap element is coupled to the attachment, and the retracting mechanism having one side acting on the actuating handle and seated with an other side on the cap element, wherein seating elements are arranged on both lateral sections of the cap element and on both lateral sections of the actuating handle which in a form of a separable bearing pin/bearing eye connection form a pivot axis between the actuating handle and the cap element.

2. In the breast pump in accordance with claim 1, wherein in a completely inserted state of the pump piston, a stroke chamber opening on a side of the stroke chamber facing away from the breast connection element is covered by an upper section of the actuating handle which in a position of use is located above a pivot axis.

3. In the breast pump in accordance with claim 2, wherein in a rear area remote from the breast attachment element the cap element has a rounded top which in a pivoted-in state of an upper section of the actuating handle makes a steady transition into the curved exterior of the actuating handle.

4. In the breast pump in accordance with claim 2, wherein the stroke chamber in the cap element is curved in an arc-shape in accordance with a movement path of the pump piston which is actuated by an upper section of the actuating handle.

5. In the breast pump in accordance with claim 4, wherein with the container attached, a pivot path of the upper section of the actuating handle near a connection to the pump piston is selected so large that in a moved-out state at least an upper edge section of the pump piston is outside of an upper opening edge of the stroke chamber opening.

6. In the breast pump in accordance with claim 5, wherein a retracting mechanism has at least one tension spring, a suspension element is positioned on the actuating handle, and a further suspension element is positioned on the cap element so that with an inserted piston position a direction of a tensile force lies above a pivot axis of the actuating handle at least until with the container attached the actuating handle reaches a maximum pivot angle in a retraction direction of the pump piston, and with the container removed and with a further increased pivot angle the direction of the tensile force is below the pivot axis so that the actuating handle is maintained in an opened position in relation to the cap element.

7. In the breast pump in accordance with claim 5, wherein the retracting mechanism has at least one pressure spring, a support element on an inside of the actuating handle and a support section at the cap element are positioned so that at least with a piston rod inserted, a direction of force of pressure lies below the pivot axis of the actuating handle.

8. In the breast pump in accordance with claim 7, wherein the pressure spring is a spiral spring with a front suspension lug suspended and retained in a support section of a free end section of the retaining element which is oriented downward when in use and arcs upward in a U-shape in an interior chamber of the cap element and the attachment and is supported with a free end section bent from the suspension lug on a support element arranged on an inside of the actuating handle.

9. In the breast pump in accordance with claim 8, wherein an electric pump is directly connected with a hose to the connecting sleeve arranged on the attachment or to the connecting bore.

10. In the breast pump in accordance with claim 9, wherein a connecting point between one of the connecting sleeve and the connecting bore and the cap element is sealed by one of a conical connection and a seal ring.

11. In the breast pump in accordance with claim 10, wherein an opening is provided on the attachment near the connecting sleeve or the connection bore, which can be closed by one of a stopper and a hand.

12. In the breast pump in accordance with claim 1, wherein the stroke chamber in the cap element is curved in an arc-shape in accordance with a movement path of the pump piston which is actuated by an upper section of the actuating handle.

13. In the breast pump in accordance with claim 1, wherein with the container attached, a pivot path of an upper section of the actuating handle near a connection to the pump piston is selected so large that in a moved-out state at least an upper edge section of the pump piston is outside of an upper opening edge of the stroke chamber opening.

14. In the breast pump in accordance with claim 1, wherein a retracting mechanism has at least one tension spring, a suspension element is positioned on the actuating handle and a further suspension element is positioned on the cap element so that with an inserted piston position a direction of a tensile force lies above a pivot axis of the actuating handle at least until with the container attached the actuating handle reaches a maximum pivot angle in a retraction direction of the pump piston and with the container removed and with a further increased pivot angle the direction of the tensile force is below the pivot axis so that the actuating handle is maintained in an opened position in relation to the cap element.

15. In the breast pump in accordance with claim 1, wherein a retracting mechanism has at least one pressure spring, a support element on an inside of the actuating handle and a support section at the cap element are positioned so that at least with a piston rod inserted, a direction of force of pressure lies below the pivot axis of the actuating handle.

16. In the breast pump in accordance with claim 15, wherein the pressure spring is a spiral spring with a front suspension lug suspended and retained in a support section of a free end section of the retaining element which is oriented downward when in use and arcs upward in a U-shape in an interior chamber of the cap element and the attachment and is supported with a free end section bent from the suspension lug on a support element arranged on an inside of the actuating handle.

17. In the breast pump in accordance with claim 1, wherein an electric pump is directly connected with a hose to the connecting sleeve arranged on the attachment or to the connecting bore.

18. In the breast pump in accordance with claim 1, wherein a connecting point between one of the connecting sleeve and the connecting bore and the cap element is sealed by one of a conical connection and a seal ring.

19. In the breast pump in accordance with claim 1, wherein an opening is provided on the attachment near one of the connecting sleeve and the confection bore, which can be closed by one of a stopper and a hand.

20. In the breast pump in accordance with claim 1, wherein the snap-in element is embodied as snap-in tongue which is oriented toward the container with a free end section which, in the attached state, extends with a snap-in section behind an edge of the attachment facing toward the container when the cap element located opposite the snap-in tongue is pushed on one of the connecting sleeve and the connecting bore, which are oriented axis-parallel in relation to the container.

21. In the breast pump in accordance with claim 1, wherein a cross section of an upper section and a lower section of the actuating handle are each outwardly rounded on a rear facing away from the breast attachment element and make a steady transition into each other, and an obtuse angle open toward the rear is formed between the upper section and the lower section.

22. In the breast pump in accordance with claim 1, wherein spacer cams which contact an upper edge of the container in an attached state are on an inside of a screw connector of the attachment for connecting with the container so that an air exchange with an atmosphere is provided in the attached state.

23. In the breast pump in accordance with claim 1, wherein the pump piston has a piston rod with a backward oriented end section having a releasable hinged connecting with an upper section of the actuating handle.

24. In the breast pump in accordance with claim 1, wherein the manual pump unit and the attachment are arranged so that a weight of each is compensated, and in an empty state with the attachment placed on and the manual pump unit attached the container remains upright.

25. In the breast pump in accordance with claim 1, wherein a secondary air regulating unit which can be operated manually from an outside is on the cap element for ventilating a section chamber which varies during a pump operation.

26. In the breast pump in accordance with claim 25, wherein the secondary air regulating unit has at least one of a rotatable insert and an attachment arranged on an exterior of the cap element which when rotated a flow-through conduit which leads through a wall in the cap element into the stroke chamber is one of opened and closed.

27. In a breast pump having an attachment releasably applied to an opening of a container and having a breast attachment element and a manual pump unit which is releasably connected to the attachment by a connecting sleeve or a connecting bore having a cap-shaped connecting section, and a pump piston which can be moved back and forth in a stroke chamber with an actuating handle, which is pivotable and has a retracting mechanism, the improvement comprising:

the cap-shaped connecting section and the stroke chamber combined in a mutual cap element which is fixed on the attachment by a retaining means, the retracting mechanism having one side acting on the actuating handle and seated with an other side on the cap element in a completely inserted state of the pump piston, a stroke chamber opening on a side of the stroke chamber facing away from the breast connection element covered by an upper section of the actuating handle which in a position of use is located above a pivot axis, the stroke chamber in the cap element curved in an arc-shape in accordance with a movement path of the pump piston which is actuated by an upper section of the actuating handle with the container attached, a pivot path of the upper section of the actuating handle near a connection to the pump piston selected so large that in a moved-out state at least an upper edge section of the pump piston is outside of an upper opening edge of the stroke chamber opening the retracting mechanism having at least one pressure spring, a support element on an inside of the actuating handle and a support section at the cap element positioned so that at least with a piston rod inserted, a direction of force of pressure lies below the pivot axis of the actuating handle, the pressure spring being a spiral spring with a front suspension lug suspended and retained in a support section of a free end section of the retaining element which is oriented downward when in use and arcs upward in a U-shape in an interior chamber of the cap element and the attachment and is supported with a free end section bent from the suspension lug on a support element arranged on an inside of the actuating handle, an electric pump directly connected with a hose to the connecting sleeve arranged on the attachment or to the connecting bore, a connecting point between one of the connecting sleeve and the connecting bore and the cap element sealed by one of a conical connection and a seal ring, an opening provided on the attachment near the connecting sleeve or the connection bore, which can be closed by one of a stopper and a hand, and the retaining means having a snap-in element which snaps together with the attachment when the cap element is coupled to the attachment.

28. In the breast pump in accordance with claim 27, wherein the snap-in element is embodied as a snap-in tongue which is oriented toward the container with a free end section which, in the attached state, extends with a snap-in section behind an edge of the attachment facing toward the container when the cap element located opposite the snap-in tongue is pushed on one of the connecting sleeve and the connecting bore, which are oriented axis-parallel in relation to the container.

29. In the breast pump in accordance with claim 28, wherein an interior of the cap element has one of retaining flaps and ribs on both sides which form guide elements when placed on the attachment and securing elements against twisting of the cap element in relation to the attachment.

30. In the breast pump in accordance with claim 29, wherein in a rear area remote from the breast attachment element the cap element has a rounded top which in the pivoted-in state of the upper section of the actuating handle makes a steady transition into the curved exterior of the actuating handle.

31. In the breast pump in accordance with claim 30, wherein a cross section of the upper section and the lower section are each outwardly rounded on a rear facing away from the breast attachment element and make a steady transition into each other, and an obtuse angle open toward the rear is formed between the upper section and the lower section.

32. In the breast pump in accordance with claim 31, wherein an intermediate piece is insertable into a V-shaped gap which when the actuating handle is pivoted is formed in the upper area between the upper section and an edge of the stroke chamber opening by which a stroke travel of the pump piston is preset to be one of continuous and stepped.

33. In the breast pump in accordance with claim 32, wherein spacer cams which contact the upper edge of the container in the attached state are on an inside of a screw connector of the attachment for connecting with the container so that an air exchange with an atmosphere is provided in the attached state.

34. In the breast pump in accordance with claim 33, wherein the pump piston has a piston rod with a backward oriented end section having a releasable hinged connection with the upper section of the actuating handle.

35. In the breast pump in accordance with claim 34, wherein a protrusion made of a soft material is arranged on the interior on a container side of the lower section of the actuating handle forming a stop between the actuating handle and the container.

36. In the breast pump in accordance with claim 35, wherein the manual pump unit and the attachment are arranged so that a weight of each is compensated, and in the empty state with the attachment placed on and the manual pump unit attached the container remains upright.

37. In the breast pump in accordance with claim 36, wherein a secondary air regulating unit which can be operated manually from an outside is on the cap element for ventilating a section chamber which varies during a pump operation.

38. In the breast pump in accordance with claim 37, wherein the secondary air regulating unit has at least one of a rotatable insert and an attachment arranged on an exterior of the cap element which when rotated a flow-through conduit which leads through a wall in the cap element into the stroke chamber is one of opened and closed.

39. In a breast pump having an attachment releasably applied to an opening of a container and having a breast attachment element and a manual pump unit which is releasably connected to the attachment by a connecting sleeve or a connecting bore having a cap-shaped connecting section, and a pump piston which can be moved back and forth in a stroke chamber with an actuating handle which is pivotable and has a retracting mechanism the improvement comprising:
the cap-shaped connecting section and the stroke chamber combined in a mutual cap element which is fixed on the attachment by a retaining means having a snap-in element snapped together with the attachment when the cap element is coupled to the attachment, and
the retracting mechanism having one side acting on the actuating handle and seated with an other side on the cap element wherein an interior of the cap element has one of retaining flaps and ribs on both sides which form guide elements when placed on the attachment and securing elements against twisting of the cap element in relation to the attachment.

40. In the breast pump in accordance with claim 39, wherein seating elements are arranged on both lateral sections of the cap element and on both lateral sections of the actuating handle which in a form of separable bearing pin/bearing eye connection form a pivot axis between the actuating handle and the cap element.

41. In a breast pump having an attachment releasably applied to an opening of a container and having a breast attachment element and a manual pump unit which is releasably connected to the attachment by a connecting sleeve or a connecting bore having a cap-shaped connecting section, and a pump piston which can be moved back and forth in a stroke chamber with an actuating handle which is pivotable and has a retracting mechanism, the improvement comprising:
the cap-shaped connecting section and the stroke chamber combined in a mutual cap element which is fixed on the attachment by a retaining means having a snap-in element snapped together with the attachment when the cap element is coupled to the attachment, and
the retracting mechanism having one side acting on the actuating handle and seated with an other side on the cap element wherein an intermediate piece is insertable into a V-shaped gap which when the actuating handle is pivoted is formed in an upper area between an upper section of the actuating handle and an edge of the stroke chamber opening by which a stroke travel of the pump piston is preset to be one of continuous and stepped.

42. In the breast pump in accordance with claim 41, wherein seating elements are arranged on both of the lateral sections of the cap element and on both lateral sections of the actuating handle which in a form of separable bearing pin/bearing eye connection form the pivot axis between the actuating handle and the cap element.

43. In a breast pump having an attachment releasably applied to an opening of a container and having a breast attachment element and a manual pump unit which is releasably connected to the attachment by a connecting sleeve or a connecting bore having a cap-shaped connecting section, and a pump piston which can be moved back and forth in a stroke chamber with an actuating handle which is pivotable and has a retracting mechanism, the improvement comprising:
the cap-shaped connecting section and the stroke chamber combined in a mutual cap element which is fixed on the attachment by a retaining means having a snap-in element snapped together with the attachment when the cap element is coupled to the attachment, and
the retracting mechanism having one side acting on the actuating handle and seated with an other side on the cap element wherein a protrusion made of a soft material is arranged on the interior on a container side of a lower section of the actuating handle forming a stop between the actuating handle and the container.

* * * * *